(12) United States Patent
Sugiura

(10) Patent No.: US 7,118,561 B2
(45) Date of Patent: Oct. 10, 2006

(54) CORNEAL SURGERY APPARATUS

(75) Inventor: Motohiro Sugiura, Gamagori (JP)

(73) Assignee: Nidek Co., Ltd., (JP)

(*) Notice: Subject to any disclaimer, the term of this patent is extended or adjusted under 35 U.S.C. 154(b) by 0 days.

(21) Appl. No.: 10/649,699

(22) Filed: Aug. 28, 2003

(65) Prior Publication Data
US 2004/0044333 A1 Mar. 4, 2004

(30) Foreign Application Priority Data
Aug. 29, 2002 (JP) ............................. 2002-250494

(51) Int. Cl.
*A61F 9/08* (2006.01)
(52) U.S. Cl. ............................................. 606/5; 606/4
(58) Field of Classification Search ................ 128/898; 606/4–6
See application file for complete search history.

(56) References Cited

U.S. PATENT DOCUMENTS

| | | | |
|---|---|---|---|
| 5,507,799 A | 4/1996 | Sumiya | |
| 5,520,679 A | 5/1996 | Lin | |
| 5,620,436 A | 4/1997 | Lang et al. | |
| 5,632,742 A | 5/1997 | Frey et al. | |
| 5,637,109 A | 6/1997 | Sumiya | |
| 5,752,950 A * | 5/1998 | Frey et al. | 606/12 |
| 5,827,264 A | 10/1998 | Hobla | |
| 5,865,832 A * | 2/1999 | Knopp et al. | 606/10 |
| 5,906,608 A | 5/1999 | Sumiya et al. | |
| 6,033,075 A | 3/2000 | Fujieda et al. | |
| 6,086,204 A | 7/2000 | Magnante | |
| 6,159,202 A | 12/2000 | Sumiya et al. | |
| 6,203,539 B1 | 3/2001 | Shimmick et al. | |
| 6,210,401 B1 | 4/2001 | Lai | |
| 6,299,307 B1 * | 10/2001 | Oltean et al. | 351/210 |
| 6,315,773 B1 * | 11/2001 | Frey et al. | 606/12 |
| 6,467,907 B1 | 10/2002 | Fujieda et al. | |
| 6,666,857 B1 * | 12/2003 | Smith | 606/12 |
| 6,702,806 B1 * | 3/2004 | Gray et al. | 606/5 |
| 2001/0024265 A1 | 9/2001 | Fujieda | |
| 2002/0082590 A1 * | 6/2002 | Potgieter | 606/4 |
| 2003/0120266 A1 * | 6/2003 | Fujieda | 606/5 |
| 2004/0054359 A1 * | 3/2004 | Ruiz et al. | 606/5 |
| 2004/0143245 A1 * | 7/2004 | Gray et al. | 606/5 |
| 2005/0119642 A1 * | 6/2005 | Grecu et al. | 606/5 |

FOREIGN PATENT DOCUMENTS

| | | |
|---|---|---|
| JP | 2003-79657 A1 | 3/2003 |
| WO | EP 0850614 A2 * | 12/1997 |
| WO | EP 0983757 A2 * | 9/1999 |
| WO | EP 1138290 A1 * | 3/2001 |
| WO | WO 01/28476 A1 | 4/2001 |

* cited by examiner

*Primary Examiner*—Henry M. Johnson, III
(74) *Attorney, Agent, or Firm*—Rader, Fishman & Grauer PLLC

(57) ABSTRACT

A corneal surgery apparatus capable of accurately obtaining torsion information on an eyeball or positional information on an eye even during laser irradiation or after a cornea is incised into a layer, and of accurately performing corneal surgery with a laser beam. The apparatus, for ablating a cornea of a patient's eye by irradiation of a laser beam, includes an irradiation optical system for irradiating the laser beam onto the cornea, an image-pickup device for picking up an image of an anterior-segment of the eye, a mark detection device for processing the obtained image of the anterior-segment and detecting a mark provided to the eye, a reference position setting device for setting a reference position in which the mark being detected is to be positioned, and a torsion detection device for obtaining torsion information on the eye based on the detected mark and the set reference position.

6 Claims, 6 Drawing Sheets

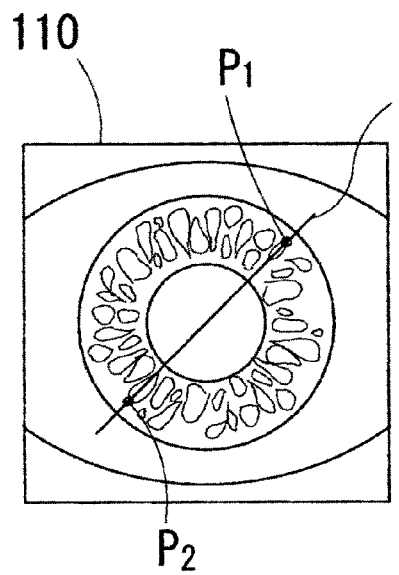
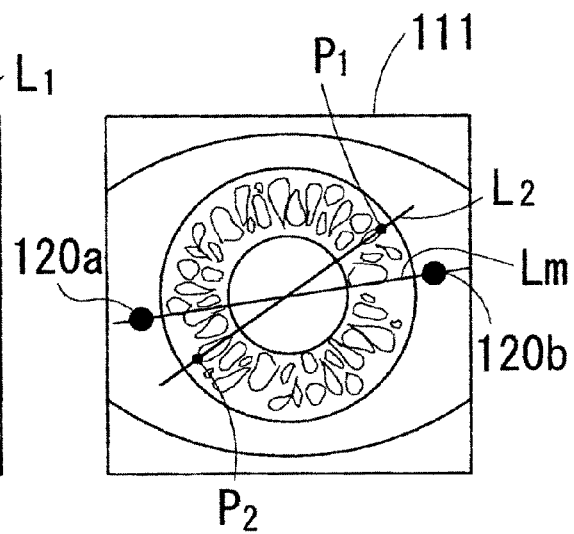
FIG. 7A    FIG. 7B
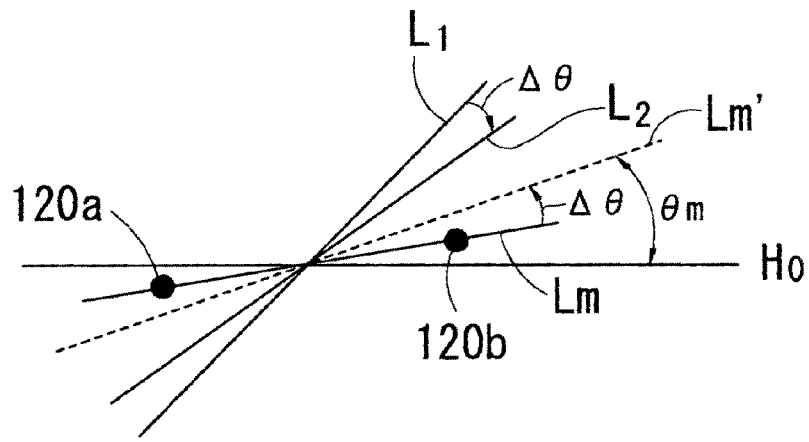
FIG. 8

CORNEAL SURGERY APPARATUS

BACKGROUND OF THE INVENTION

1. Field of the Invention

The present invention relates to a corneal surgery apparatus which ablates a cornea to change a surface shape of the cornea.

2. Description of Related Art

Conventionally, there is known a corneal surgery apparatus which ablates a cornea by irradiation of a laser beam and changes a surface shape of the cornea to correct a refractive error of an eye. In this kind of surgery, characteristics such as a corneal shape and eye refractive power distribution (or distribution of wave aberration) of a pre-operative patient's eye (eye to be operated on) are measured, and data on corneal ablation is obtained based on the measurement data.

A position (attitude) of the patient at the time of the measurement for obtaining the data on the corneal ablation is generally sitting or standing (a state where the patient's eye faces forward). On the other hand, a position (attitude) of the patient at the time of the corneal surgery is generally lying on his/her back (a state where the patient's eye faces upward). It is known that, in the case of the eye which faces upward contrary to the eye which faces forward, torsion (rotation) of an eyeball occurs. Therefore, there is proposed an optical system for adjusting a condition of the eyeball, which differs at the time of the measurement before the surgery and at the time of the surgery, utilizing an iris image of the eye.

However, during the laser irradiation, or in LASIK surgery (Laser in Situ Keratomileusis) in which an epithelium is incised into a layer to form a corneal flap and then the laser irradiation is performed, the iris image is difficult to obtain since the corneal surface becomes rough. In this case, the torsion information itself on the eyeball is not obtained, or even if obtained, its accuracy gets worse. In addition, also in the case of obtaining positional information on the eye utilizing the iris image, same problems are presented.

SUMMARY OF THE INVENTION

An object of the invention is to overcome the problems described above and to provide a corneal surgery apparatus capable of accurately obtaining torsion information on an eyeball or positional information on an eye even during laser irradiation or after a cornea is incised into a layer, and of accurately performing corneal surgery with a laser beam.

To achieve the objects and in accordance with the purpose of the present invention, a corneal surgery apparatus has an irradiation optical system for irradiating the laser beam onto the cornea, an image-pickup device for picking up an image of an anterior-segment of the eye, a mark detection device for processing the obtained image of the anterior-segment and detecting a mark provided to the eye, a reference position setting device for setting a reference position in which the mark being detected is to be positioned; and a torsion detection device for obtaining torsion information on the eye based on the detected mark and the set reference position.

In another aspect of the present invention, a corneal surgery apparatus has an irradiation optical system for irradiating the laser beam onto the cornea, an image-pickup unit which picks up an image of an anterior-segment of the eye, a mark detection unit which processes the obtained image of the anterior-segment and detects a mark provided to the eye, a reference position setting unit which sets a reference position in which the mark being detected is to be positioned, and a torsion detection unit which obtains torsion information on the eye based on the detected mark and the set reference position.

Additional objects and advantages of the invention are set forth in the description which follows, are obvious from the description, or may be learned by practicing the invention. The objects and advantages of the invention may be realized and attained by the corneal surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 7A and 7B are views showing an example of an image of the anterior-segment at the time of measurement inputted from the ophthalmic measurement apparatus and an example of that at the time of surgery picked up by a camera in the corneal surgery apparatus; and FIG. 8 is a view illustrating a method for setting a reference position for the mark.

DETAILED DESCRIPTION OF THE PREFERRED EMBODIMENTS

Figure 1:
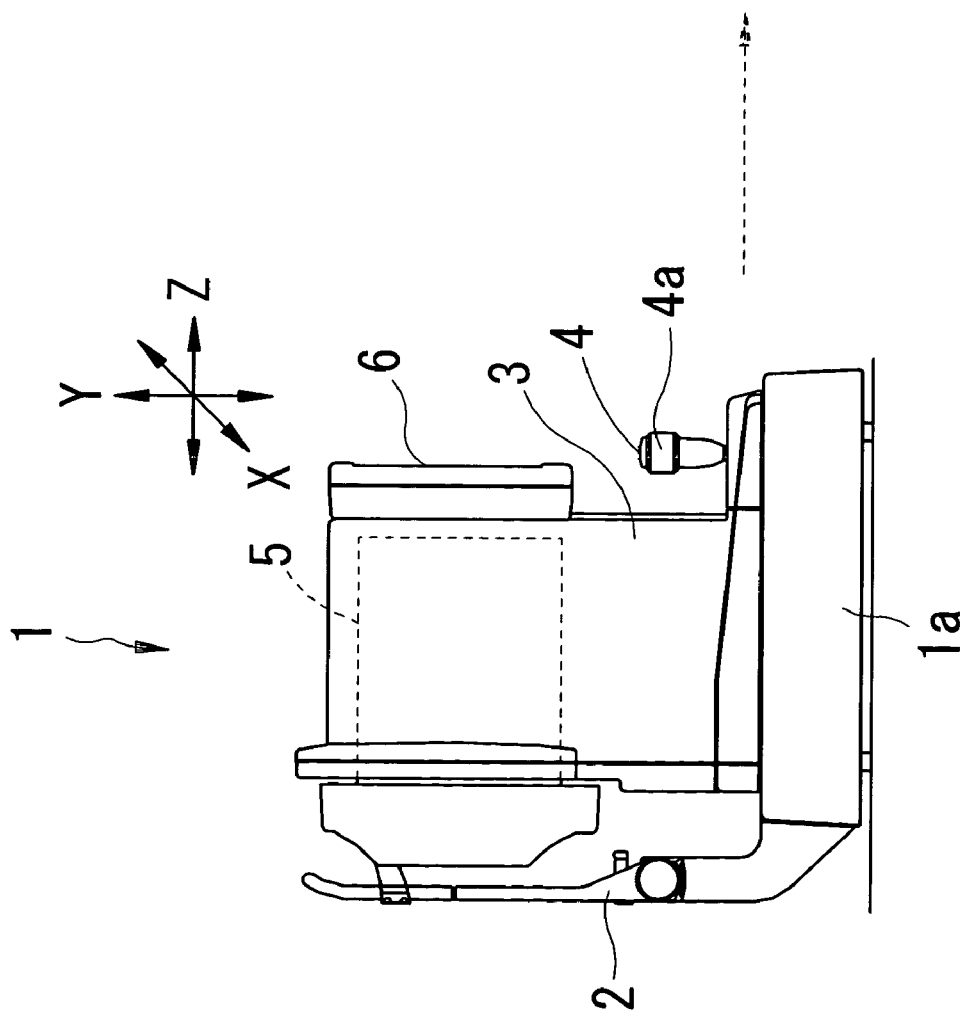
FIG. 1 is a view showing a schematic configuration of a corneal surgery apparatus system consistent with the present invention.

A detailed description of one preferred embodiment of a corneal surgery apparatus embodied by the present invention is provided below with reference to the accompanying drawings. FIG. 1 is a view showing a schematic configuration of a corneal surgery apparatus system consistent with the present invention. An ophthalmic measurement apparatus 1 measures a corneal shape and eye refractive power distribution of a patent's eye. A corneal surgery apparatus 200 irradiates a laser beam onto the patient's eye. The measurement apparatus 1 obtains measurement data on the corneal shape and the eye refractive power distribution that become factors for determining a corneal ablation amount, and then obtains data on corneal ablation amount distribution based on the measurement data. Further, the measurement apparatus 1 picks up an image of an anterior-segment of the patient's eye at the time of the measurement. The data on the corneal ablation amount distribution and data on the image of the anterior-segment are transferred via cable communication or electronic recording media to a computer 209 in the surgery apparatus 200.

FIG. 1 shows an outer appearance of the measurement apparatus 1 when viewed from its side. Attached to a fixed base 1a is a head support part 2 for holding a patent's head. The measurement is performed while a patient's face is placed approximately upright on the head support part 2 (the patient's eye faces forward). A measurement unit 5 houses a measurement optical system, an alignment optical system and the like. When a joystick 4 is tilted in right/left and back/forth directions (X and Z directions), a main body 3 equipped with the measurement unit 5 is moved in the right/left and back/forth directions (X and Z directions) on the fixed base 1a. In addition, when a rotation knob 4a placed on the joystick 4 is operated to rotate, an up/down driving mechanism comprised of a motor and the like is activated, and the measurement unit 5 is moved in an up/down direction (Y direction) with respect to the main body 3. A color monitor (display) 6 displays information for a surgeon such as an image of the patient's eye for observation, alignment information, and measurement results.

Figure 2:
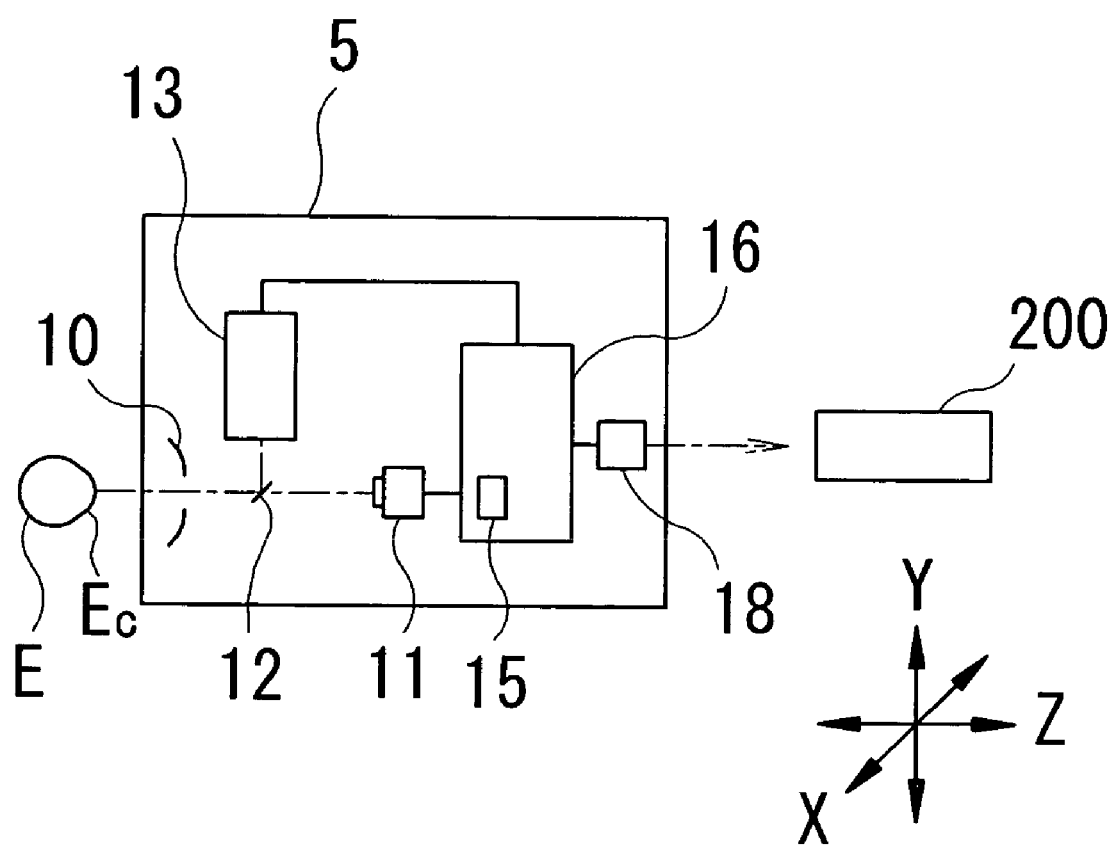
FIG. 2 is a view showing a schematic configuration of a measurement system and a control system in an ophthalmic measurement apparatus.

FIG. 2 is a view showing a schematic configuration of a measurement system and a control system in the measurement apparatus 1. The measurement unit 5 in the measurement apparatus 1 is provided with a projection optical system 10 which projects a number of circular placido rings onto a cornea Ec of the patient's eye E, a camera unit 11 which picks up an image of the placido rings projected onto the cornea Ec and an image of an anterior-segment of the eye E, a half mirror 12, an eye refractive power distribution measurement optical system 13, an analysis unit 16 having a memory 15 which stores the images picked up by the camera unit 11, and communication means 18. The camera unit 11 picks up the image of the anterior-segment in a condition where the placido rings are projected onto the cornea Ec and that in a condition where they are not projected thereonto. When the image of the anterior-segment is picked up, the anterior-segment of the eye E is illuminated by an illumination light source not illustrated.

The eye refractive power distribution measurement optical system 13 is provided with an optical system which scans slit light to a fundus of the eye E, and a detection optical system having a plurality of pairs of photodetectors which are placed symmetrically with respect to an optical axis in an approximately conjugate position with the cornea Ec in a meridian direction which corresponds to a slit direction of the slit light.

The analysis unit 16 has a capability of processing the images of the placido rings stored in the memory 15 to obtain corneal curvature distribution as a corneal shape, and obtaining refractive power distribution of the eye E varying in the meridian direction based on a signal outputted from the photodetectors provided in the eye refractive power distribution measurement optical system 13. Further, the analysis unit 16 has a capability of obtaining data on the corneal ablation amount distribution for keratorefractive surgery from the data on the corneal curvature distribution and that on the eye refractive power distribution. The method thereof will be described hereinafter. The eye refractive power distribution is converted to refractive power distribution at a corneal position, and refractive power distribution required for making the eye E emmetropia is obtained as a value represented in a form of a corneal refractive power. Then, the obtained refractive power distribution is converted to corneal curvature distribution by the Snell's law, and a three-dimensional shape is obtained. And then, data on a surgical area is provided thereto, and the three-dimensional shape obtained through the refractive power distribution measurement is subtracted from the three-dimensional shape of the pre-operative cornea obtained through the corneal shape measurement to obtain ablation amount distribution. The ablation amount distribution is obtained being divided into a spherical component (a rotationally symmetrical component), a cylindrical component (a linearly symmetrical component), and an asymmetric component, and each ablation amount distribution is graphically displayed in a three-dimensional shape such as a bird's eye view.

The details on the constitution and the method for the corneal shape measurement and the eye refractive power distribution measurement, and on the analytical method performed by the analysis unit 16 are provided in Japanese Patent Application Unexamined Publication No. Hei 11-342152 corresponding to U.S. Pat. No. 6,033,075, so please refer to it for detail. The data on the corneal ablation amount distribution obtained by the analysis unit 16 is transferred to the computer 209 in the corneal surgery apparatus 200 by the communication means 18 communicating via wire communication or wireless communication (a flexible disk and the like).

Figure 3:
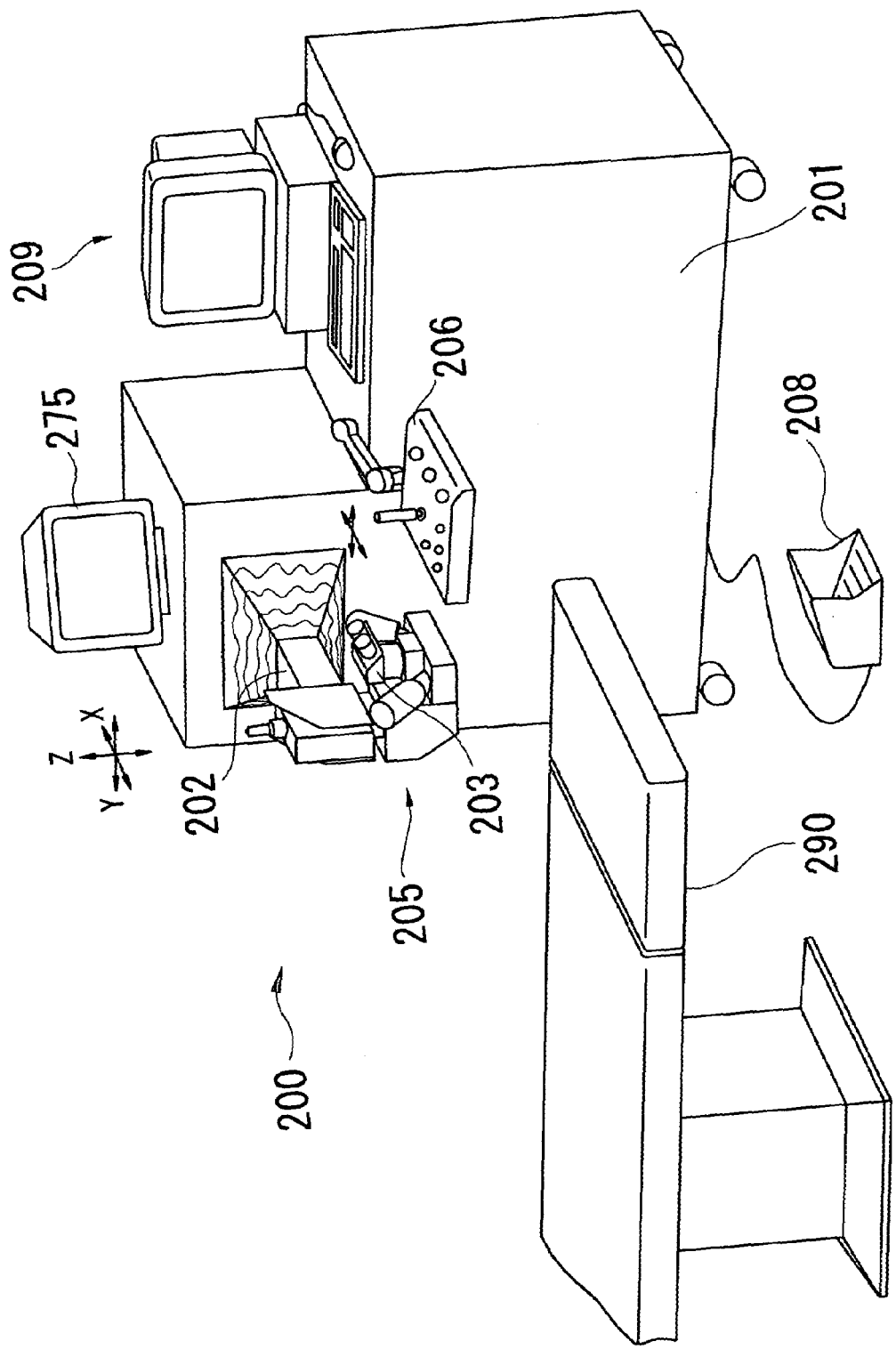
FIG. 3 is a schematic external view of a corneal surgery apparatus.
Figure 4:
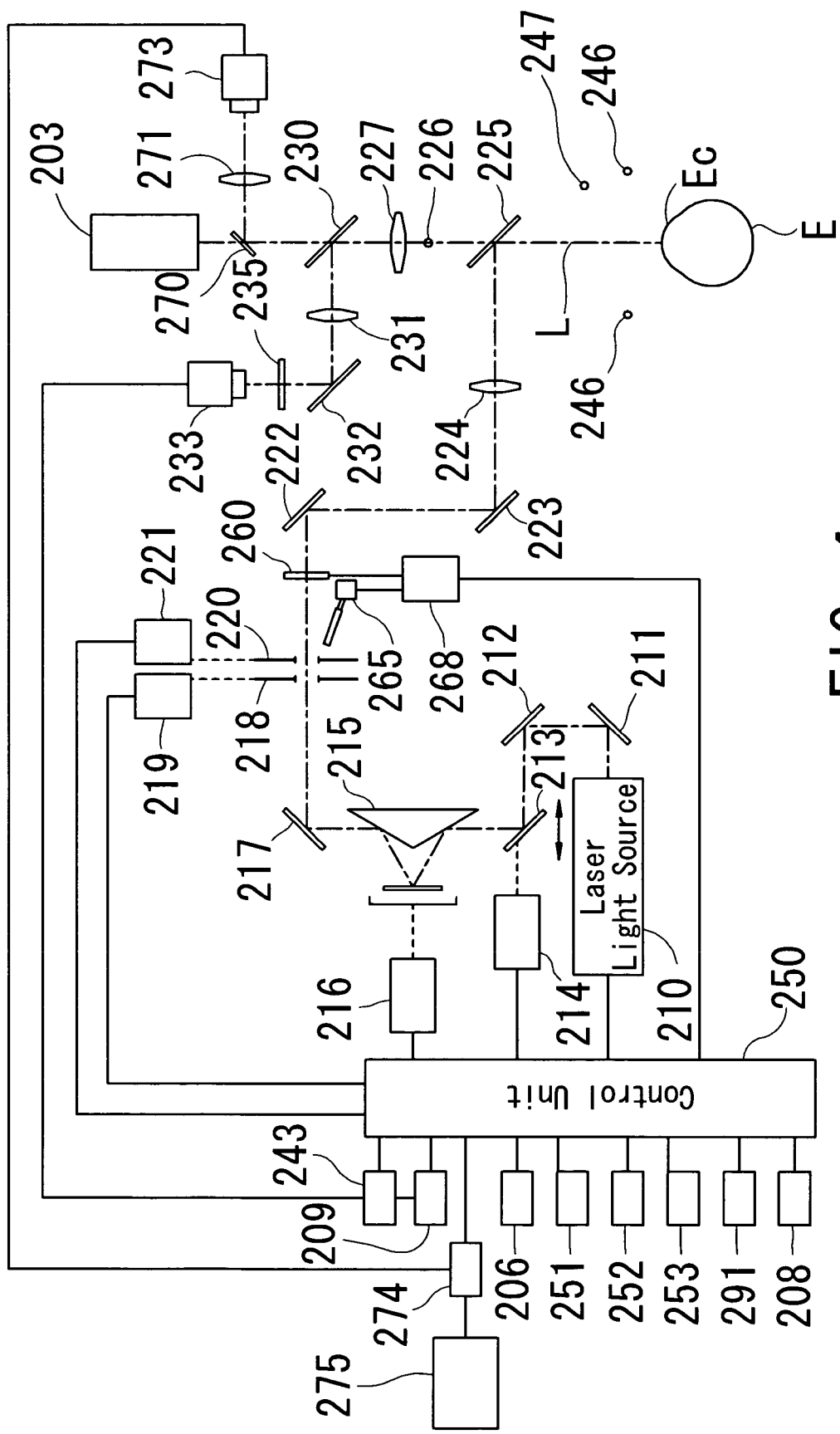
FIG. 4 is a view showing a schematic configuration of a laser irradiation optical system and a control system in the corneal surgery apparatus.

FIG. 3 is a schematic external view of the surgery apparatus 200, and FIG. 4 is a view showing a schematic configuration of a laser irradiation optical system and a control system in the surgery apparatus 200.

A laser beam emitted from an excimer laser source 210 disposed inside a main body 201 of the surgery apparatus 200 is transmitted through optical systems such as mirrors and guided to an arm unit 202. The arm unit 202 is movable in X and Y directions shown in FIG. 3. In addition, a tip portion 205 of the arm unit 202 is movable in a Z direction. The movement in each direction is performed by driving units 251, 252 and 253 comprised of a motor, a sliding mechanism and the like. Arranged on a controller 206 are a joystick and various switches. A footswitch 208 transmits a trigger signal for the laser irradiation. The computer 209 inputs various data for a necessary surgical condition, and performs calculation, display, storage and the like of data on laser irradiation control. A color monitor (display) 275 displays an image of the patient's eye for observation. The patient undergoes the surgery while being recumbent on a bed 290 (the patient's eye faces upward). The patient's eye is placed under a microscope unit 203 attached to the tip portion 205. Besides, the bed 290 is rotatable in a horizontal direction by a bed rotation mechanism 291.

In FIG. 4, the laser beam emitted from the laser source 210 is reflected by mirrors 211 and 212, and further reflected by a plane mirror 213. The mirror 213 is translatable (movable) in the direction of the arrow shown in FIG. 4 by a mirror driving unit 214, so that the laser beam may be translated (scanned) in the Gaussian direction to uniformly ablate an object. In this regard, Japanese Patent Application Unexamined Publication No. Hei 4-242644 corresponding to U.S. Pat. No. 5,507,799 describes in detail, so please refer to it for detail.

An image rotator 215 is driven and rotated about a central optical axis L as its center by an imager rotator driving unit 216, and the laser beam is rotated about the optical axis L. Reference numeral 217 is a mirror.

A circular aperture 218 with a circular opening limits an ablation area to a circular shape, and its opening diameter is changed by an aperture driving unit 219. A slit aperture 220 with a slit opening limits the ablation area to a slit shape, and its opening width and opening direction are changed by an aperture driving unit 221. Mirrors 222 and 223 change the direction of the beam. A projecting lens 224 projects the openings of the circular aperture 218 and/or the slit aperture 220 onto the cornea Ec.

In addition, a dividing aperture plate 260 including a plurality of small circular apertures is insertably and removably disposed on an optical path between the slit aperture 220 and the mirror 222. The dividing aperture plate 260 further limits the ablation area (an irradiation area) in combination with a dividing shutter 265. Shutter plates of the dividing shutter 265 cover and uncover the small apertures in the dividing aperture plate 260 selectively, thereby enabling the ablation area (the irradiation area) to be further limited for the laser irradiation. The dividing aperture plate 260 and the dividing shutter 265 are translatable (movable) within a plane vertical to the optical axis L and rotatable about the optical axis L by a driving unit 268.

A dichroic mirror 225 has a property of reflecting an excimer laser beam and transmitting visible light and infrared light. The laser beam passed through the projecting lens 224 is reflected by the dichroic mirror 225, and is directed to and irradiated onto the cornea Ec.

Placed above the dichroic mirror 225 are a fixation light 226, an objective lens 227, a dichroic mirror 230 which reflects infrared light and transmits visible light, and a microscope unit 203. The eye E is illuminated by a visible light source 247, and a surgeon observes the eye E through the microscope unit 203. On an optical path on the reflecting side of the dichroic mirror 230, an image forming lens 231, a mirror 232, an infrared light transmission filter 235, and a CCD camera 233 for infrared photographing are sequentially arranged. The camera 233 picks up the image of the anterior-segment illuminated by an infrared light source 246. The output of the camera 233 is connected to an image processing unit 243. The image processing unit 243 detects a pupil position by processing the photographed image of the anterior-segment. Further, the image processing unit 243 detects an iris image, an image of a mark previously provided to the eye E and the like.

In addition, a half mirror 270 is arranged in a position that is above the dichroic mirror 230 and between binocular paths of the microscope unit 203 (on an optical axis of the objective lens 227). Arranged on an optical path on the reflecting side of the half mirror 270 are an image forming lens 271 and a CCD camera 273 for visible photographing. The camera 273 picks up the image of the anterior-segment illuminated by the visible light source 247. The output of the camera 273 is connected to an image control unit 274, and the image control unit 274 is connected with the color monitor 275. The color monitor 275 displays the picked up image of the anterior-segment.

A control unit 250 controls the laser source 210 and each of the driving units. The control unit 250 is connected with the computer 209, the image processing unit 243, the image control unit 274, the controller 206, the footswitch 208 and the like.

Ablation performed by the surgery apparatus 200 will be briefly described hereinafter. In the case of ablation for myopic correction so as to remove the spherical component, the ablation is performed in the following manner. The laser beam is moved (scanned) in the Gaussian distribution direction by moving the mirror 213 within the opening of the circular aperture 218. Then, every time the laser beams has been moved (scanned) in one direction, the moving (scanning) direction of the laser beam is changed by the rotation of the image rotator 215, and the approximately uniform ablation is performed within the opening of the circular aperture 218. This is performed every time the opening diameter of the circular aperture 218 is sequentially changed. Thereby, the ablation of the spherical component is performed deeply at the central part of the cornea Ec and shallowly at the peripheral part.

In the case of ablation so as to remove the cylindrical component, the opening diameter of the circular aperture 218 is fixed in agreement with an optical zone. Further, the opening direction of the slit aperture 220 is adjusted so that its opening width changes in the direction of a steepest meridian of the ablation data. Then, as is the case with the ablation of the spherical component mentioned above, the laser beam is moved (scanned) by moving the mirror 213, and every time the laser beam has been moved (scanned) in one direction, the moving (scanning) direction of the laser beam is changed by the rotation of the imager rotator 215, and the approximately uniform ablation is performed within the opening of the slit aperture 220. This is performed every time the opening width of the slit aperture 220 is sequentially changed. Thus, the ablation of the cylindrical component may be performed.

In the case of partial ablation so as to remove the asymmetric component, the dividing aperture plate 260 is used. The dividing aperture plate 260 is arranged on the optical path of the laser beam to control positions of the small apertures in the dividing aperture plate 260, and to selectively open and close the small apertures by driving the dividing shutter 265. By the movement (scanning) of the laser beam caused by the movement of the mirror 213, the laser beam of a small area passing through the opening small apertures is partially irradiated onto the cornea Ec.

Figure 5:
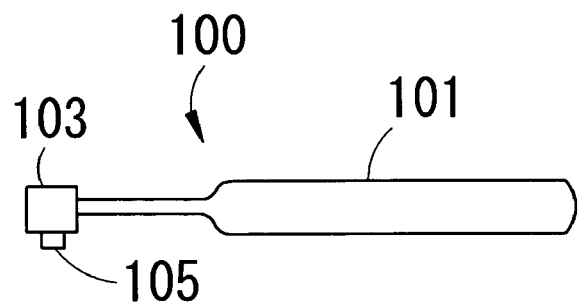
FIGS. 5A and 5B are views illustrating an example of a marking unit which provides a patient's eye with a mark for detecting a torsion condition of an eyeball.
Figure 5:
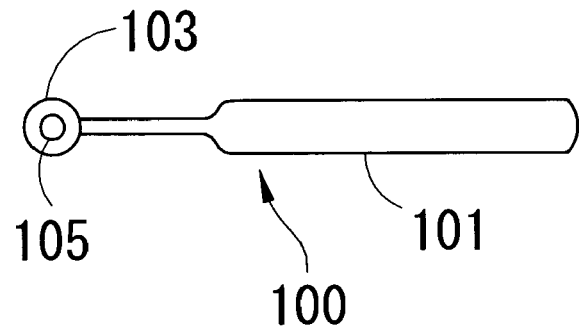

FIGS. 5A and 5B are views illustrating an example of a marking unit which provides the eye E with a mark for detecting the torsion condition of the eyeball. FIG. 5A shows a side view of a marking unit 100, and FIG. 5B shows a view when the marking unit 100 shown in FIG. 5A is viewed from beneath. A marking member 105 is attached to a support base 103 on the tip of a grasping part 101. The marking member 105 is, for example, in a circular shape of about 1 mm in diameter. The marking member 105 is made of somewhat soft felt into which red or black coloring ink is previously impregnated. Such a mark on a sclera of the eye E facilitates visible observation (photographing). Further, also at the time of the infrared photographing, the sclera part and the marked part are differentiated from each other to enable the mark detection. The eye E is provided with marks so as to specify its directivity.

Next, an operation of the system with the constitution as above will be described. Firstly, the measurement apparatus 1 measures the corneal curvature distribution as the corneal shape and the eye refractive power distribution. The corneal curvature distribution and the eye refractive power distribution are obtained as data in which a horizontal direction of the eye is taken as an axial angle reference. On the occasion of the measurement, the patient's head is fixed by the head support part 2 so that both of the patient's eyes are horizontally positioned. The patient's face is made in an upright state. The analysis unit 16 obtains the data on the corneal ablation amount distribution based on the corneal curvature distribution and the eye refractive power distribution. The data on the corneal ablation amount distribution is also obtained as the data in which the horizontal direction of the eye is taken as the axial angle reference. In addition, the camera unit 11 picks up the image of the anterior-segment of the eye E at the time of the measurement, and the image data is stored in the memory 15. The data on the corneal ablation amount distribution and the data on the image of the anterior-segment are transferred to the computer 209 in the surgery apparatus 200.

Figure 6:
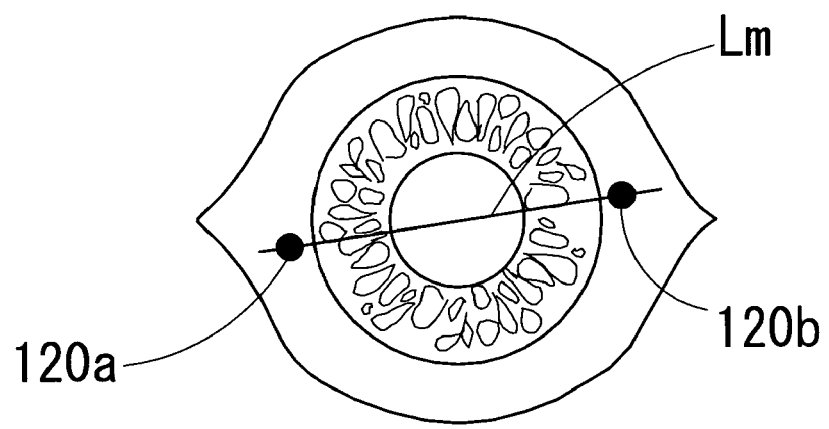
FIG. 6 is a view showing an example of marks provided to an anterior-segment of the patient's eye.

Secondly, the surgery apparatus 200 ablates the cornea Ec based on the data on the corneal ablation amount distribution. Before the laser irradiation, the marking unit 100 provides a mark to the eye E. When the mark is provided to the patient being recumbent on the bed 209, the microscope unit 203 may be used to observe the eye E. More than two marks are preferably provided in positions on the sclera, having the ablation area therebetween, on a somewhat outer side of the corneal rim. FIG. 6 is an example thereof, wherein two marks 120a and 120b are provided on the somewhat outer side of the corneal rim. A line segment Lm connecting the marks 120a and 120b is taken as an axial direction at the time of mark detection. Incidentally, the two (or more) marks are not necessarily provided in line in a horizontal direction at the time of the observation, but they may be provided so that the direction of the line segment Lm is detectable. In addition, when the marks are provided, the observation may be made with a slit lamp while the patient's face is in the upright state as is the case with the measurement.

After the eye E is provided with the marks, the surgeon observes the eye E through the microscope unit 203, and performs alignment for the laser irradiation so that a reticle center and a pupil center of the eye E observed within the microscope unit 203 coincide with each other. The alignment may also be performed automatically. The camera 233 picks up the image of the anterior-segment of the eye E, and its image signal is inputted to the image processing unit 243. The image processing unit 243 detects an edge position of the pupil to obtain the position of the pupil center. The control unit 250 controls the driving units 251, 252 and 253 based on an detection signal on the position of the pupil center, and moves the arm unit 202 (see Japanese Patent Application Unexamined Publication No. Hei 9-149914 corresponding to U.S. Pat. No. 6,159,202 for detail). Also when the eye E moves, the position of the pupil center is detected to perform tracking by moving the arm unit 202.

Further, based on the image of the anterior-segment at the time of the surgery picked up by the camera 233 and that at the time of the measurement inputted from the measurement apparatus 1, the image processing unit 243 obtains information on an positional relationship of the axial direction of the marks with respect to the axial angle reference of the measurement data to determine a reference position (a reference direction) in which the marks are to be positioned at the time of the surgery.

FIG. 7A is a view showing an example of the image of the anterior-segment at the time of the measurement inputted from the measurement apparatus 1. FIG. 7B is a view showing an example of the image of the anterior-segment at the time of the surgery picked up by the camera 233 in the surgery apparatus 200, and this image includes images of the marks 120a and 120b provided to the eye E. The image processing unit 243 detects characteristic points common to an image 110 of the anterior-segment at the time of the measurement and an image 111 of the anterior-segment at the time of the surgery. For example, it is assumed that common characteristic points P1 and P2 are detected among each of iris patterns of the images 110 and 111. A line segment L1 connecting the characteristic points P1 and P2 for the image 110 and a line segment L2 connecting the characteristic points P1 and P2 for the image 111 are respectively obtained. Then, as shown in FIG. 8, a horizontal reference direction H0 for the image 110 and that for the image 111 are aligned (the axial angle reference for the measurement data and that for the laser irradiation optical system are aligned), and a comparison between the direction of the line segment L1 and that of the line segment L2 is made to obtain an torsion error $\Delta\theta$ of the image 111 with respect to the image 110 at the time of the measurement. When the torsion error $\Delta\theta$ is obtained, many characteristic points common to the images 110 and 111 are preferably extracted to average and obtain the torsion error between each of the images.

Further, the image processing unit 243 detects the images of the marks 120a and 120b from the image 111, and obtains the direction of the line segment Lm connecting each of those images. The torsion error $\Delta\theta$ is offset with respect to the direction of the line segment Lm to obtain the direction of a line segment Lm'. The direction of the line segment Lm' is obtained as an angle $\theta$m with respect to the horizontal reference direction H0. The angle $\theta$m makes the information on the positional relationship of the marks 120a and 120b with respect to the axial angle reference at the time of the measurement. At the same time, the horizontal reference direction of the image 11 may be aligned with the horizontal reference direction H0 to obtain a reference direction in which the images of the marks 120a and 120b detected at the time of the surgery are to be positioned. The image processing unit 243 stores that reference direction into a memory in the control unit 250. When the surgery is in progress, the torsion error to be corrected is obtained as an angle difference of the axial direction of the detected images of the marks (the direction of the line segment Lm) with respect to the reference angle $\theta$m. Besides, while the iris image is obtained, the torsion error may be obtained by the detection of the characteristic points P1 and P2, and when the iris image becomes undetectable, the torsion error may be detected based on the detection result on the images of the marks 120a and 120b.

In the foregoing description, the image of the anterior-segment provided with the marks 120a and 120b are obtained using the camera 233 in the surgery apparatus 200. However, the present invention is not limited thereto. For example, an image-pickup apparatus, attached to the measurement apparatus 1 or the slit lamp, may pick up the image of the anterior-segment provided with the marks 120a and 120b before the surgery, and its image data may be inputted to the computer 209 and used. In the case of using the measurement apparatus 1, the alignment is performed as is the case with the measurement, and then the camera unit 11 picks up the image of the anterior-segment provided with the marks 120a and 120b. The image data is transferred to the computer 209. The computer 209 detects the images of the marks 120a and 120b, and obtains the direction of the line segment Lm with respect to the horizontal reference direction. Since the image of the anterior-segment may be assumed to have the same positional relationship as that at the time of the measurement of the corneal shape and the eye refractive power distribution, the direction of the detected line segment Lm may be directly treated as the reference direction in which the images of the marks 120a and 120b are to be positioned. Incidentally, if the image of the anterior-segment in the same condition as that at the time of the measurement is not obtained by the measurement apparatus 1 and the like, the positional relationship of the marks 120a and 120b with the axial angle reference of the measurement data may be obtained by the above-described method.

Further, the characteristic points P1 and P2 may not only be detected through the image processing by the computer 209 (as well in the case of the image processing unit 243) but also be specified by the surgeon. For example, the monitor in the computer 209 may display the image of the anterior-segment at the time of the measurement and that at the time of the surgery provided with the marks 120a and 120b to specify the characteristic points common to both the images using instruction means such as a mouse.

Furthermore, in the case of obtaining the image of the anterior-segment provided with the marks 120a and 120b before the surgery using the image-pickup apparatus attached to the measurement apparatus 1 or the slit lamp, an external computer may perform processing for obtaining the positional relationship of the measurement data with the marks 120a and 120b, and only a result thereof may be inputted to the computer 209 in the surgery apparatus 200 to determine the reference position for the marks 120a and 120b.

Next, a method for correcting the torsion error will be described. The correction is performed by a method of moving the patient's head with respect to the laser irradiation optical system, and that of rotating the laser irradiation position while the patient's head is fixed.

Firstly, the method for correcting the torsion error by moving the patient's head will be described. Displayed on the display of the monitor 275 are the image of the anterior-segment of the eye E and a numerical value which expresses the angle of the detected torsion error $\Delta\theta$. For example, if the torsion error is generated clockwise, an angle with a sign "+" is displayed, and if counterclockwise, an angle with a sign "−" is displayed. The surgeon corrects the torsion error by moving the patient's head so that the value 0 is displayed. Incidentally, when the surgeon makes correction while observing the eye E through the microscope unit 203, an assistant or the like may support the surgeon by orally passing the information on the angle of the torsion error displayed on the monitor 275 to the surgeon. Otherwise, a head up display may be used, which has a constitution where light from a display device for displaying the information on the torsion error is guided to the observation optical system of the microscope unit 203 to synthesize the observed image and the light from the display device. This enables the surgeon to know the information on the torsion error while the surgeon himself/herself keeps observing through the microscope unit 203. When the alignment and the correction of the torsion error have been completed, the footswitch 208 is pressed to irradiate the laser beam onto the eye E.

If the torsion of the eyeball occurs during the laser irradiation, since the laser irradiation has already been provided, the detection of the iris image becomes difficult. In this case, the information on the torsion error is obtained based on the marks 120a and 120b provided outside the ablation area. On the occasion of necessity for the correction of the torsion error, the control unit 250 suspends the laser irradiation. As the information on the torsion error is displayed on the monitor 275 and the like, the surgeon moves the patient's head again in accordance with that information to correct the torsion error. After the completion of the correction, the laser irradiation is restarted. Incidentally, the patient's head may be moved by rotating the bed 290 by the actuation of the bed rotation mechanism 291 through the control of the control unit 250.

Next, the correction of the torsion error by rotating the laser irradiation position presented by the laser irradiation optical system will be described. The information on the torsion error obtained by the image processing unit 243 is transferred to the control unit 250. In the ablation of the cylindrical component, the control unit 250 rotates the axial direction (the opening direction) of the slit aperture 220 so as to make correction by the amount of the torsion error so that the irradiation position of the laser beam is rotated with respect to the optical axis L. In the ablation of the asymmetric component, the dividing aperture plate 260 is rotated with respect to the optical axis L by the amount of the torsion error.

Further, in a case where the torsion of the eyeball occurs during the laser irradiation, the control unit 250 rotates the slit aperture 220 or the dividing aperture plate 260 based on the information on the torsion error transferred from the image processing unit 243 so that the laser irradiation position tracks the torsion of the eyeball. At this time, the image processing unit 243 obtains the information on the torsion error based on the marks 120a and 120b. If the torsion error amount is beyond a permissible range of the tracking, the control unit 250 suspends the laser irradiation and restarts it when the torsion error is corrected.

Incidentally, also in the case of the tracking by the laser irradiation position in association with the displacement of the eye, when the position of the pupil center becomes difficult to detect (or from the beginning), the information on the displacement may be obtained based on the marks 120a and 120b so that the arm unit 202 may be moved based on that information. For example, as is the case with the tracking based on the position of the pupil center, when the alignment of the laser irradiation position with respect to the eye E has been completed, the positions of the marks 120a and 120b are stored in the memory in the control unit 250. After that, the control unit 250 compares the positions of the marks 120a and 120b detected by the camera 233 with the positions stored in the memory at all times to obtain the information on the displacement. The control unit 250 drives and controls the driving units 251 and 252 based on the obtained information on the displacement, and moves the arm unit 202 to move the laser irradiation position in the X and Y directions.

The method of utilizing the marks 120a and 120b previously provided to the eye E may be applied to LASIK surgery. In the LASIK surgery, a corneal incision apparatus called a microkeratome incises an epithelium in a layer to prepare a corneal flap while one end of the cornea is left, and provides the laser irradiation onto a corneal stroma after the corneal flap is opened. When the corneal flap is opened, the incised surface becomes rough, so that the detection of the iris image becomes difficult, as in the case during the laser irradiation, as well. Therefore, the iris image and the images of the marks 120a and 120b are detected from an image of the anterior-segment before the corneal flap preparation or that in a condition where the prepared corneal flap is temporarily put back on, and as in FIG. 8, the positional relationship of the direction in which the marks 120a and 120b when the patient's position is in the measurement state are to be positioned with respect to the laser irradiation optical system in the surgery apparatus 200 is kept stored. The detection of the torsion error thereafter is performed based on the marks 120a and 120b.

In the foregoing preferred embodiment, the images of the marks 120a and 120b are detected from the image of the anterior-segment picked up by the camera 233. However, those images may be detected from the image of the anterior-segment picked up by the camera 273. In this case, if the image-pickup centers obtained by the cameras 233 and 273 are aligned with the horizontal reference direction, both the images may be treated as equivalent. The iris image is detected from the image of the anterior-segment picked up by the camera 233 so as to adjust with the image from the measurement apparatus 1.

Further, in the foregoing preferred embodiment, the example of providing the marks 120*a* and 120*b* to the sclera of the eyeball has been described. However, the present invention is not limited thereto. For example, there is a surgery method of performing the laser irradiation while a ring-shaped sheet (a sheet having a circular opening larger than the ablation area) for water absorption covers the eyeball at the time of the surgery. If the mark cannot be provided to the sclera due to the use of the ring-shaped sheet, the marks 120*a* and 120*b* may be provided to the ring-shaped sheet. The ring-shaped sheet covering the eyeball rotates in agreement with the torsion of the eyeball, so that the information on the torsion error may be obtained based on the marks 120*a* and 120*b* as described above. In this manner, the marks provided to the anterior-segment of the eyeball include those provided to the ring-shaped sheet.

Furthermore, in the foregoing preferred embodiment, the characteristic points common to the image of the anterior-segment at the time of the measurement and that at the time of the surgery are detected based on the iris pattern. However, the present invention is not limited thereto. For example, the characteristic points in the shape of the pupil rims may be utilized.

In addition, the laser irradiation optical system may include a scanning mirror (which may be constituted of two galvano-mirrors and the like) for scanning the laser beam formed in a small spot of about 0.1 to 1.0 mm two-dimensionally in the X and Y directions. When the torsion error is corrected by rotating the laser irradiation position using this type of optical system, the angle reference axis (X and Y axes) of the control data for the scanning mirror may be rotated by the amount of the torsion error. In addition, also for the displacement of the eye, as described above, the scanning mirror may be driven and controlled to move the laser irradiation position in the X and Y directions.

As described above, according to the present invention, even during the laser irradiation or after the cornea is incised in a layer, the torsion information on the eyeball and the positional information on the eye may be obtained accurately, so that the corneal surgery with the laser beam may be performed more accurately.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus for ablating a cornea of a patient's eye by irradiation of a laser beam, the apparatus comprising:
    an irradiation optical system for irradiating the laser beam onto the cornea;
    input means for inputting a first anterior-segment image of the eye picked up in a condition where measurement data for determining corneal ablation data is obtained;
    image-pickup means for picking up a second anterior-segment image of the eye in a condition where the laser beam is irradiated, the second anterior-segment image including images of marks for torsion-detection provided outside an ablation area of the eye;
    characteristic point detection means for detecting characteristic points common to the first anterior-segment image and the second anterior-segment image;
    mark detection means for detecting the mark images in the second anterior-segment image;
    torsion-detection means for automatically obtaining a torsion-error angle of the eye; and
    torsion-correction means for automatically correcting the obtained torsion-error angle,
    wherein the torsion-detection means automatically obtains, based on the characteristic points in the first anterior-segment image and the characteristic points in the second anterior segment image picked up before the corneal ablation, a first torsion-error angle that occurred before the corneal ablation,
    the torsion-correction means automatically performs any one of rotation of a patient's head and correction of control data on the irradiation optical system based on the obtained first torsion-error angle so as to correct the obtained first torsion-error angle,
    the torsion-detection means automatically obtains, based on the mark images in the second anterior-segment image picked up before the corneal ablation after correction of the first torsion-error angle and the mark images in the second anterior segment image picked up during the corneal ablation, a second torsion-error angle that occurred during the corneal ablation, the torsion-correction means automatically performs any one of rotation of the patient's head while stopping the irradiation of the laser beam and correction of the control data on the irradiation optical system based on the obtained second torsion-error angle so as to correct the obtained second torsion-error angle.

2. The corneal surgery apparatus according to claim 1, further comprising display means for displaying the first and second anterior-segment images,
    wherein the characteristic point detection means includes designation means for designating the characteristic points based on the displayed images.

3. The corneal surgery apparatus according to claim 2, further comprising an irradiation control means for controlling the irradiation of the laser beam,
    wherein the irradiation control means stops the irradiation of the laser beam when the obtained second torsion-error angle is beyond a permissible range.

4. The corneal surgery apparatus according to claim 1, further comprising an irradiation control means for controlling the irradiation of the laser beam,
    wherein the irradiation control means stops the irradiation of the laser beam when the obtained second torsion-error angle is beyond a permissible range.

5. A corneal surgery apparatus for ablating a cornea of a patient's eye by irradiation of a laser beam, the apparatus comprising:
    an irradiation optical system for irradiating the laser beam onto the cornea;
    an input unit which inputs a first anterior-segment image of the eye picked up in a condition where measurement data for determining corneal ablation data is obtained;
    an image-pickup unit which picks up a second anterior-segment image of the eye in a condition where the laser beam is irradiated, the second anterior-segment image including images of marks for torsion-detection provided outside an ablation area of the eye;
a characteristic point detection unit which detects characteristic points common to the first anterior-segment image and the second anterior-segment image;
a mark detection unit which automatically detects the mark images in the second anterior-segment image;
a torsion-detection unit which automatically obtains a torsion-error angle of the eye; and
a torsion-correction unit which automatically corrects the obtained torsion-error angle,
wherein the torsion-detection unit automatically obtains, based on the characteristic points in the first anterior-segment image and the characteristic points in the second anterior-segment image picked up before corneal ablation, a first torsion-error angle that occurred before the corneal ablation,
the torsion-correction unit automatically performs any one of rotation of a patient's head and correction of control data on the irradiation optical system so as to correct the obtained first torsion-error angle,
the torsion-detection unit automatically obtains, based on the mark images in the second anterior-segment image picked up before the corneal ablation after correction of the first torsion-error angle and the mark images in the second anterior-segment image picked up during the corneal ablation, a second torsion-error angle that occurred during the corneal ablation, and
the torsion-correction unit automatically performs any one of rotation of the patient's head while stopping the irradiation of the laser beam and correction of the control data on the irradiation optical system so as to correct the obtained second torsion-error angle.

6. The corneal surgery apparatus according to claim 5, further comprising an irradiation control unit which controls the irradiation of the laser beam.

* * * * *